US012584123B2

(12) United States Patent
Lee et al.

(10) Patent No.: US 12,584,123 B2
(45) Date of Patent: Mar. 24, 2026

(54) ELECTROMAGNETIC RADIATION METHOD AND APPARATUS FOR PERFORMING THE SAME

(71) Applicant: ELECTRONICS AND TELECOMMUNICATIONS RESEARCH INSTITUTE, Daejeon (KR)

(72) Inventors: Young Seung Lee, Daejeon (KR); Sang Bong Jeon, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 639 days.

(21) Appl. No.: 18/159,311

(22) Filed: Jan. 25, 2023

(65) Prior Publication Data

US 2024/0002830 A1     Jan. 4, 2024

(30) Foreign Application Priority Data

May 27, 2022     (KR) ........................ 10-2022-0065472

(51) Int. Cl.
*C12N 13/00*          (2006.01)
*C12M 1/00*          (2006.01)
(Continued)

(52) U.S. Cl.
CPC ............. *C12N 13/00* (2013.01); *C12M 29/24* (2013.01); *C12M 41/12* (2013.01); *G01R 29/0857* (2013.01)

(58) Field of Classification Search
CPC ....... C12N 13/00; C12M 29/24; C12M 41/12; C12M 41/14; C12M 35/02;
(Continued)

(56) References Cited

U.S. PATENT DOCUMENTS 9,407,309 B2     8/2016  Lee et al.
2012/0141552 A1*  6/2012  Dalecki ................ C12N 5/0656
                                                977/773
(Continued)

FOREIGN PATENT DOCUMENTS

EP          2319911 B1 *  4/2019  ........... C12M 37/06
KR     20-0311892 Y1     5/2003
(Continued)

OTHER PUBLICATIONS

Machine Translation of KR 20110090508 A (Year: 2025).*
(Continued)

*Primary Examiner* — Michael L Hobbs
(74) *Attorney, Agent, or Firm* — Rabin & Berdo, P.C.

(57)          ABSTRACT

Provided is an electromagnetic radiation method and an apparatus for performing the same. The electromagnetic radiation apparatus includes a signal generator configured to generate a first electromagnetic signal configured with an uplink and a downlink and scale and radiate power of the first electromagnetic signal in order to evaluate the first electromagnetic signal as a second electromagnetic signal configured only with a downlink, and a radiation chamber in which cell containers configured with cells are arranged in a circle in order to evenly irradiate a scaled first electromagnetic signal to the cells.

18 Claims, 6 Drawing Sheets

300

(51) Int. Cl.
    *C12M 1/34*         (2006.01)
    *G01R 29/08*       (2006.01)

(58) Field of Classification Search
    CPC ............ G01R 29/0857; G01R 29/0821; G01R 29/0835; G01R 29/0871
    See application file for complete search history.

(56)          References Cited

U.S. PATENT DOCUMENTS

| | | | |
|---|---|---|---|
| 2013/0267003 A1 * | 10/2013 | Goodwin | C12N 5/0062 |
| | | | 435/173.1 |
| 2016/0262652 A1 | 9/2016 | Lee et al. | |
| 2019/0393968 A1 * | 12/2019 | Ioffe | H04B 17/101 |

FOREIGN PATENT DOCUMENTS

| | | | | |
|---|---|---|---|---|
| KR | 20050008641 A | | 1/2005 | |
| KR | 10-2011-0090508 A | | 8/2011 | |
| KR | 20110090508 A | | 8/2011 | |
| KR | 1020110090508 | * | 8/2011 | ............ C12M 41/14 |
| KR | 10-1354118 B1 | | 2/2014 | |
| KR | 20160107816 A | | 9/2016 | |
| KR | 20190063168 A | | 6/2019 | |
| KR | 10-2020-0068235 A | | 6/2020 | |

OTHER PUBLICATIONS

Adnan Majeed "Comparative Studies of 3G, 4G & 5G Mobile Network & Data Offloading Method a Survey" International Journal of Research in Information Technology. vol. 3, Issue 5, pp. 421-427. May 2015 (Year: 2015).*

Ae-Kyoung Lee et al., "Review of Existing Research on the Effects of Human Exposure to RF EMF", The Journal of Korean Institute of Electromagnetic Engineering and Science. Oct. 2021.; 32(10), 857¤871.

\* cited by examiner

300

ELECTROMAGNETIC RADIATION METHOD AND APPARATUS FOR PERFORMING THE SAME

CROSS-REFERENCE TO RELATED APPLICATION

This application claims the benefit of Korean Patent Application No. 10-2022-0065472 filed on May 27, 2022, in the Korean Intellectual Property Office, the entire disclosure of which is incorporated herein by reference for all purposes.

BACKGROUND

1. Field of the Invention

One or more embodiments relate to an electromagnetic radiation method and an apparatus for performing the same.

2. Description of the Related Art

A cell experiment refers to a basic experiment for analyzing impacts of an electromagnetic wave to a human body. In a cell experiment, a cell may be exposed to an electromagnetic wave of a specific strength to observe impacts of the electromagnetic wave to the cell. The fifth-generation (5G) new radio (NR) is radio access technology developed for mobile networks. There may be concerns about impacts of a 5G NR signal on the human body.

The above description is information the inventor(s) acquired during the course of conceiving the present disclosure, or already possessed at the time, and is not necessarily art publicly known before the present application was filed.

SUMMARY

The fifth-generation (5G) new radio (NR) signal may have a flexible transmission structure in which an uplink and a downlink can be arbitratily allocated within a frequency band. Therefore, simulating impacts of a 5G NR signal on a human body may be very complex.

Embodiments may evaluate the 5G NR signal having the flexible transmission structure as a signal configured only with a downlink, through a power scaling.

By evaluating the 5G NR signal having the flexible transmission structure as the signal configured only with the downlink to calculate a specific absorption rate (SAR) of a cell, embodiments may improve easiness and reliability of a cell experiment.

Embodiments may expose a cell to a 5G NR signal stably for a long time by maintaining a temperature/humidity and a carbon dioxide concentration suitable for a cell culture.

However, the technical aspects are not limited to the aforementioned aspects, and other technical aspects may be present.

According to an aspect, there is provided an electromagnetic radiation apparatus including a signal generator configured to generate a first electromagnetic signal configured with an uplink and a downlink and scale and radiate power of the first electromagnetic signal in order to evaluate the first electromagnetic signal as a second electromagnetic signal configured only with a downlink, and a radiation chamber in which cell containers configured with cells are arranged in a circle in order to evenly irradiate a scaled first electromagnetic signal to the cells.

The electromagnetic radiation apparatus may further include a controller configured to control the signal generator, wherein the signal generator may be configured to amplify and radiate power of the scaled first electromagnetic signal under control by the controller.

The first electromagnetic signal may include the fifth-generation (5G) new radio (NR) signal configured with an uplink and a downlink, and the second electromagnetic signal may include a 5G NR signal configured only with a downlink.

The signal generator may be configured to scale the power of the first electromagnetic signal by using a ratio of all symbols and downlink symbols included in one frame of the first electromagnetic signal.

The signal generator may be configured to stop operating when a size of a reflected signal generated inside the signal generator exceeds a specific level.

A bottom surface of the radiation chamber may be configured with metal.

The electromagnetic radiation apparatus may further include a incubator configured to to maintain temperature and humidity for culturing the cells.

The radiation chamber may be disposed inside the incubator.

The radiation chamber may include a fan configured to circulate air inside the incubator.

The electromagnetic radiation apparatus may further include a cooler configured to control a temperature increase of the cell containers caused by an absorption of an electromagnetic wave by the cells.

The cooler may include a pipe in which cooling water flows, and the pipe may be installed below a bottom surface of the radiation chamber.

According to an aspect, there is provided an electromagnetic radiation method including generating a first electromagnetic signal configured with an uplink and a downlink, scaling power of the first electromagnetic signal in order to evaluate the first electromagnetic signal as a second electromagnetic signal configured only with a downlink, arranging cell containers configured with cells in a circle in order to evenly irradiate a scaled first electromagnetic signal to the cells, and radiating the scaled first electromagnetic signal towards the cell containers.

The electromagnetic radiation method may further include amplifying power of the scaled first electromagnetic signal, wherein the radiating of the scaled first electromagnetic signal may include radiating an amplified first electromagnetic signal.

The first electromagnetic signal may include a 5G NR signal configured with an uplink and a downlink, and the second electromagnetic signal may include a 5G NR signal configured only with a downlink.

The scaling of the power of the first electromagnetic signal may include scaling the power of the first electromagnetic signal by using a ratio of all symbols and downlink symbols included in one frame of the first electromagnetic signal.

The electromagnetic radiation method may further include stopping the amplifying of the power of the scaled first electromagnetic signal when a size of a reflected signal generated in a process of amplifying and radiating an electromagnetic signal exceeds a specific level. The electromagnetic radiation method may further include maintaining temperature and humidity for culturing the cells.

The electromagnetic radiation method may further include controlling a temperature increase of the cell containers caused by an absorption of an electromagnetic wave by the cells.

The controlling of the temperature increase may include cooling the cell containers by disposing a pipe in which cooling water flows adjacent to bottom surfaces of the cell containers.

According to an aspect, there is provided a cell experiment system including the electromagnetic radiation apparatus of claim 1, a thermometer configured to measure a temperature of cells which changes due to an irradiation of an electromagnetic wave generated by the electromagnetic radiation apparatus to the cells, and a specific absorption rate calculation device configured to calculate a specific absorption rate of the cells. The specific absorption rate calculation device may include a memory including instructions and a processor electrically connected to the memory and configured to execute the instructions. The processor, when the instructions are executed by the processor, may be configured to calculate the specific absorption rate of the cells based on a rate of temperature change of the cells.

Additional aspects of embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
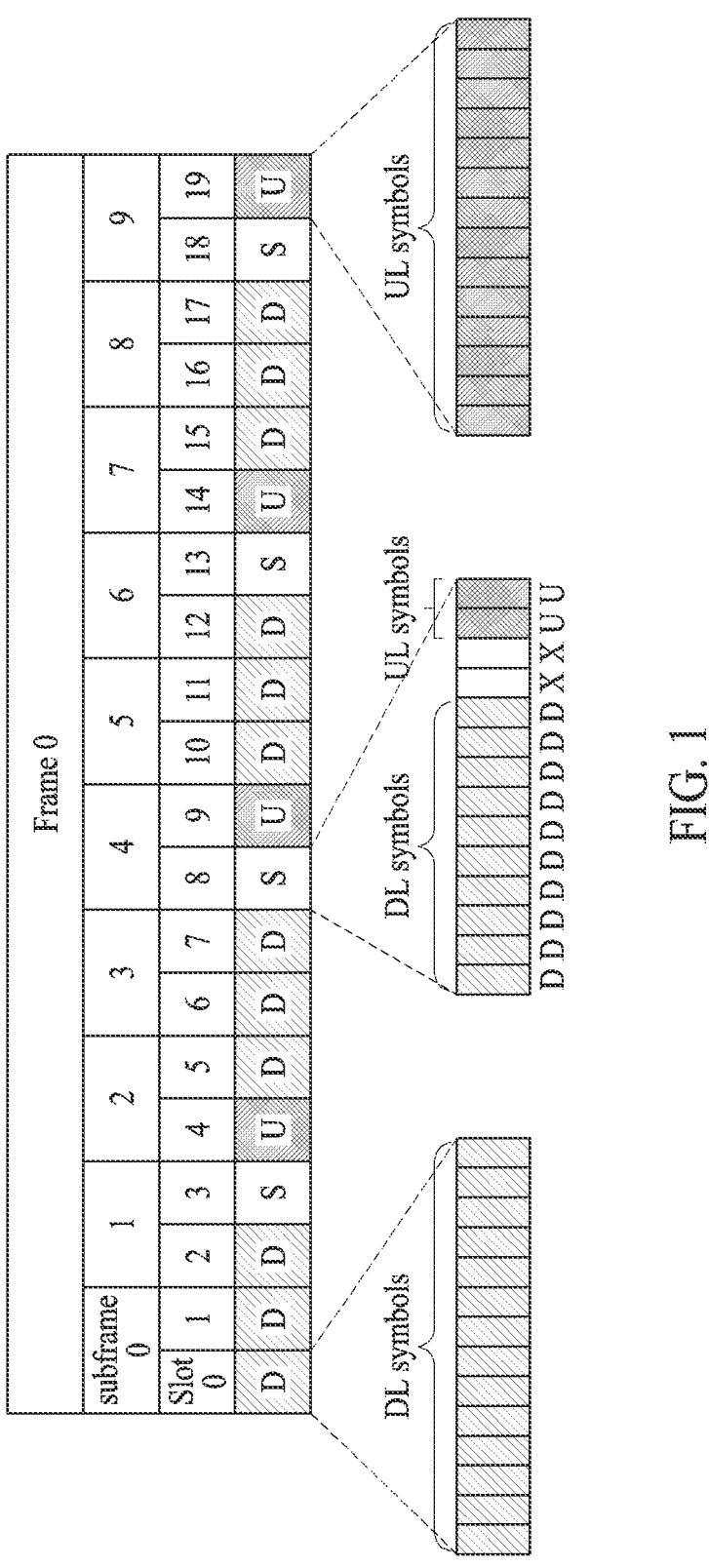
FIG. 1 is a diagram illustrating a cell experiment using the fifth-generation (5G) new radio (NR) signal according to an embodiment.

The following detailed structural or functional description is provided as an example only and various alterations and modifications may be made to the example embodiments. Here, example embodiments are not construed as limited to the disclosure and should be understood to include all changes, equivalents, and replacements within the idea and the technical scope of the disclosure.

Terms, such as first, second, and the like, may be used herein to describe various components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/including" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, embodiments will be described in detail with reference to the accompanying drawings. When describing the embodiments with reference to the accompanying drawings, like reference numerals refer to like constituent elements and a repeated description related thereto will be omitted.

FIG. 1 is a diagram illustrating a cell experiment using the fifth-generation (5G) new radio (NR) signal according to an embodiment.

Referring to FIG. 1, a 5G NR signal may have a flexible transmission structure (e.g., an uplink, a downlink, etc.) for various application services. A 5G NR signal may include a plurality of subframes in one frame. For example, one frame may include "10" subframes (0 to 9). One subframe may include a plurality of slots (e.g., time slots). For example, one subframe may include "2" time slots. Each time slot may be configured with an uplink (or uplink (UL) symbols) and a downlink (or downlink (DL) symbols)).

A cell experiment may be performed to check impacts of a 5G NR signal on a human body. A cell experiment may be an experiment in which changes in a cell is observed when the cell absorbs an electromagnetic wave of a specific value. Therefore, in the cell experiment, it may be important to control radiation power of an electromagnetic wave in order to achieve a target specific absorption rate (SAR) of the cell. A specific absorption rate may denote an amount of electromagnetic wave energy absorbed per unit mass (e.g., 1 kg, 1 g) of a biological tissue.

A specific absorption rate may be related to an electric field $\vec{E}$ absorbed by a cell layer or a temperature increase rate $$\frac{\partial T}{\partial t}$$

of a cell layer. The relation between the specific absorption rate and the electric field $\vec{E}$ absorbed by the cell layer or the temperature increase rate $$\frac{\partial T}{\partial t}$$

of the cell layer may be shown in the equation below.

$$SAR = \frac{\sigma|E|^2}{2\rho} = C\frac{\partial T}{\partial t}\Big|_{t=0}$$ [Equation 1]

In the equation, $\rho$ denotes a density of a cell layer, $\sigma$ denotes a conductivity, $C$ denotes a specific heat capacity, and $$\frac{\partial T}{\partial t}\Big|_{t=0}$$

denotes an initial temperature increase rate immediately after a cell is irradiated with an electromagnetic wave.

It may be difficult to insert a probe (e.g., a probe for measuring an electric field) into a cell experiment apparatus due to a structure (e.g., a structure of a radiation chamber and a structure of an electromagnetic wave-exposure device) of the cell experiment apparatus. Therefore, in general, a method using a temperature increase rate of a cell layer may be used to check a specific absorption rate of a cell. However, as described with reference to FIG. 2, the temperature increase rate of the cell layer may differ depending on a transmission structure of an electromagnetic wave. Therefore, for an electromagnetic wave having a flexible transmission structure, calculating a specific absorption rate by using a temperature increase rate may be complicated. For example, a 5G NR signal may have a transmission structure (e.g., an uplink and a downlink) which changes in a unit of milliseconds (ms). Therefore, in order to perform a cell experiment with a 5G NR signal, a method of checking a specific absorption rate by evaluating a 5G NR signal configured with an uplink and a downlink with a signal configured with only a downlink may be necessary.

Figure 2:
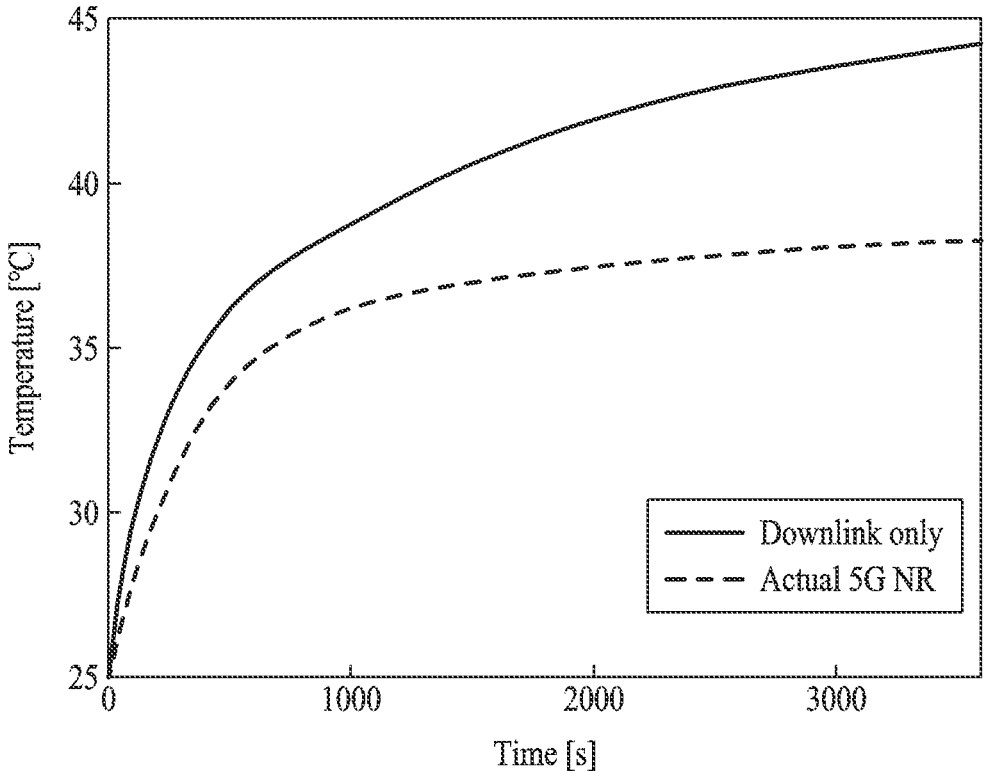
FIG. 2 is a diagram illustrating differences in a specific absorption rate rate according to a transmission structure of a 5G NR signal according to an embodiment.

FIG. 2 is a diagram illustrating differences in a specific absorption rate according to a transmission structure of a 5G NR signal according to an embodiment.

Referring to FIG. 2, when "2" kinds of electromagnetic waves (e.g., the 5G NR signal configured with the uplink and the downlink and the 5G NR signal configured with only the downlink shown in FIG. 1) are irradiated to a cell with identical radiation power, it is shown that a temperature increase rate (or a specific absorption rate) of a cell layer is different between the "2" kinds of electromagnetic waves. Specifically, it may be confirmed that a ratio of a temperature increase rate of a cell layer due to a 5G NR signal configured only with a downlink and a 5G NR signal configured with an uplink and a downlink is about 0.741. The figure may mean that radiation power of an electromagnetic wave needs to be scaled (or adjusted) in order to perform a cell experiment by evaluating a 5G NR signal configured with an uplink and a downlink as a 5G NR signal configured only with a downlink.

Figure 3:
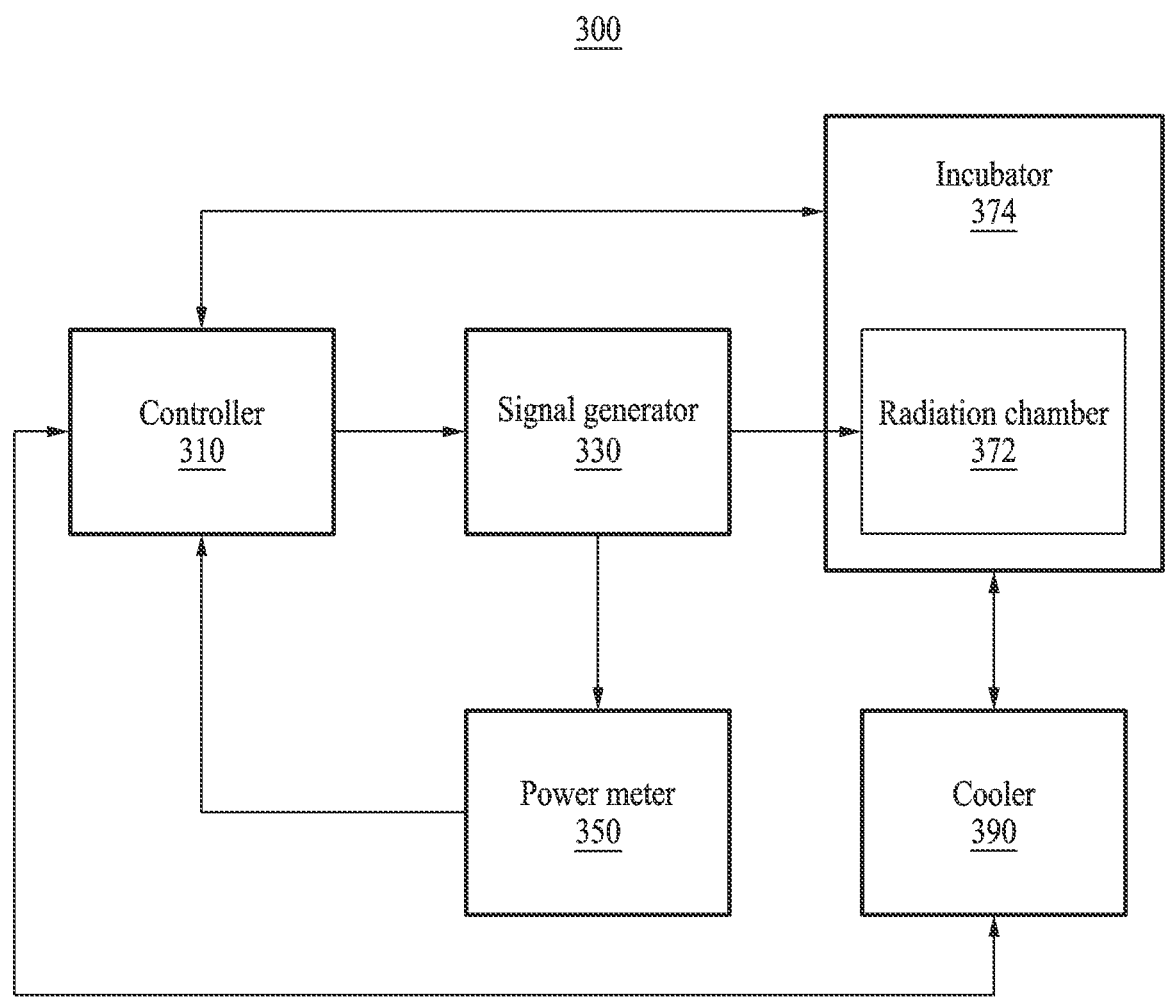
FIG. 3 is a block diagram illustrating an electromagnetic radiation apparatus according to an embodiment.

FIG. 3 is a block diagram illustrating an electromagnetic radiation apparatus according to an embodiment.

Referring to FIG. 3, according to various embodiments, an electromagnetic radiation apparatus 300 may be an apparatus for irradiating (or radiating) an electromagnetic wave (e.g., a 5G NR signal) to a cell for a cell experiment. The electromagnetic radiation apparatus 300 may include a signal generator 330, a controller 310, a power meter 350, a radiation chamber 372, a incubator 374, and a cooler 390.

According to various embodiments, the signal generator 330 may generate an electromagnetic wave (e.g., a 5G NR signal). A detailed structure of the signal generator 330 is described with reference to FIG. 4.

According to various embodiments, the controller 310 may display information (e.g., a feedback power value accumulated by the power meter 350, temperature/humidity and carbon dioxide concentration inside the incubator 374, a temperature of cooling water of the cooler 390, an electromagnetic wave exposure time of a cell, a monitoring interval, etc.) necessary for a cell experiment. The controller 310 may control operations of the signal generator 330, the incubator 374, and the cooler 390. For example, the controller 310 may transmit a control signal about a frequency and a structure (e.g., a transmission structure) of an electromagnetic wave generated by the signal generator 330 to the signal generator 330. In addition, the controller 310 may control a strength of an electromagnetic wave generated by the signal generator 330 in order to achieve a target specific absorption rate (e.g., a 5G NR signal absorption rate of a cell). For example, the controller 310 may control a strength of an electromagnetic wave by controlling radiation power of the signal generator 330.

According to various embodiments, the power meter 350 may measure power of an electromagnetic wave (e.g., a 5G NR signal) generated by the signal generator 330. The power meter 350 may receive a portion of an electromagnetic wave from the signal generator 330 to measure power of the electromagnetic wave and may transmit the measured power to the controller 310. Information of the measured power transmitted to the controller 310 may be used by the controller 310 to control the signal generator 330. For example, the controller 310 may use the information of the measured power received from the power meter 350 to control radiation power of an electromagnetic wave (e.g., a 5G NR signal) generated by the signal generator 330.

According to various embodiments, the radiation chamber 372 may be a device for irradiating an electromagnetic wave (e.g., a 5G NR signal) generated by the signal generator 330 to cell containers. A plurality of cell containers containing cells may be disposed in the radiation chamber 372. For example, cell containers may be arranged in a circle in the radiation chamber 372 so that an electromagnetic wave is evenly irradiated to the cell containers. The radiation chamber 372 may be disposed inside the incubator 374. The radiation chamber 372 may include a fan (e.g., a ventilation fan) and a hole in order to circulate air inside the incubator 374 into the radiation chamber 372.

According to various embodiments, the incubator 374 may be a device for maintaining a temperature/humidity and a carbon dioxide concentration suitable for culturing cells. The incubator 374 may control temperature/humidity and carbon dioxide concentration of air inside the incubator 374 under control by the controller 310. The incubator 374 may transmit information about temperature/humidity and carbon dioxide concentration inside the incubator 374 to the controller 310.

According to various embodiments, the cooler 390 may be a device for controlling a temperature increase of cell containers arranged in the radiation chamber 372. When a cell absorbs an electromagnetic wave, a temperature of the cell may increase (e.g., the temperature increase rate of Equation 1), possibly causing a temperature of a cell container to increase. In order to maintain a temperature (typically about 37° C.) of a cell culture fluid suitable for cell culture, the cooler 390 may control a temperature increase of a cell container. For example, the cooler 390 may include a pipe in which cooling water flows. The pipe may be installed below a bottom surface (e.g., a bottom surface formed with a metal material having a high thermal conductivity) of the radiation chamber 372 in which a cell container is arranged.

The cooler 390 may cool a cell container by circulating the cooling water in the pipe. The cooler 390 may transmit information about temperatures of a cell container and cooling water to the controller 310.

Figure 4:
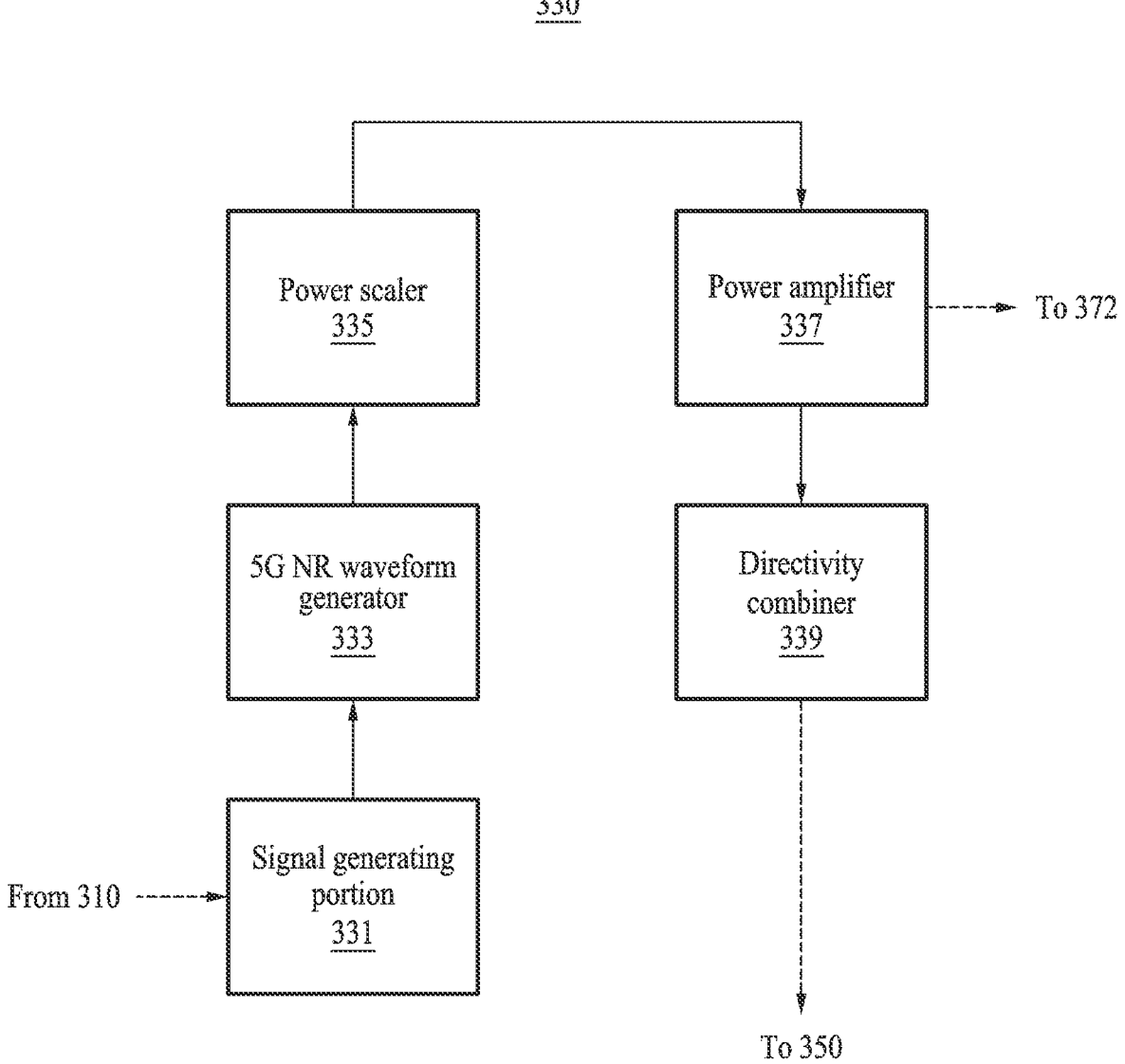
FIG. 4 is a block diagram illustrating a signal generator of FIG. 3 according to an embodiment.

FIG. 4 is a block diagram illustrating a signal generator of FIG. 3 according to an embodiment.

Referring to FIG. 4, according to various embodiments, the signal generator 330 may include a signal generating portion 331, a 5G NR waveform generator 333, a power scaler 335, a power amplifier 337, and a directivity combiner 339.

According to various embodiments, the signal generating portion 331 may generate an electromagnetic wave. For example, the signal generating portion 331 may generate an electromagnetic wave having a constant frequency and amplitude under control by the controller 310.

According to various embodiments, the 5G NR waveform generator 333 may generate a 5G NR signal by setting a flexible transmission structure (e.g., the flexible transmission structure configured with the uplink and the downlink of FIG. 1) in an electromagnetic wave generated by the signal generating portion 331.

According to various embodiments, as described above with reference to FIGS. 1 and 2, the power scaler 335 may be a device for scaling radiation power of an electromagnetic wave (e.g., a 5G NR signal) to evaluate an electromagnetic wave (e.g., a 5G NR signal) configured with an uplink and a downlink as an electromagnetic wave (e.g., a 5G NR signal) configured only with a downlink. For example, the power scaler 335 may scale radiation power by using a ratio (hereinafter, a technology duty cycle ($F_{TDC}$) of all symbols (e.g., uplink symbols and downlink symbols) and downlink symbols included in one frame of an electromagnetic wave (e.g., a 5G NR signal). A technical duty cycle ($F_{TDC}$) may be calculated using an equation as the equation below.

$$F_{TDC} = \frac{\# \text{ of downlink symbol/frame}}{\# \text{ of total symbol/frame}} \qquad \text{[Equation 2]}$$

For example, a technology duty cycle of the 5G NR signal shown in FIG. 1 is about 0.743, and the power scaler 335 may scale radiation power by using the technology duty cycle (0.743). It is shown that the technology duty cycle (0.743) is a figure very close to the temperature increase rate ratio (0.741) of the cell layer described with reference to FIG. 2. The fact that the technology duty cycle and the temperature increase rate ratio (or a specific absorption rate ratio of a cell) of the cell layer are almost identical may denote that a 5G NR signal configured with an uplink and a downlink may be evaluated as a 5G NR signal configured only with a downlink, through a scaling (e.g., a scaling using a technology duty cycle) of radiation power.

According to various embodiments, the power amplifier 337 may amplify radiation power of a scaled electromagnetic signal (e.g., a 5G NR signal) in order to achieve a target specific absorption rate (e.g., a 5G NR signal absorption rate of a cell). For example, the power amplifier 337 may amplify radiation power of a 5G NR signal scaled under control by the controller 310. The power amplifier 337 may stop a power amplification when a strength of a reflected signal generated between the power amplifier 337 and the directivity combiner 339 exceeds a specific level. An electromagnetic wave (e.g., a 5G NR signal) with radiation power amplified by the power amplifier 337 may be irradiated (or radiated) to a cell container arranged inside the radiation chamber 372.

According to various embodiments, the directivity combiner 339 may receive a portion of an electromagnetic wave (e.g., a 5G NR signal) amplified by the power amplifier 337 to transmit the portion of the electromagnetic wave to the power meter 350. A signal transmitted to the power meter 350 may be a feedback signal necessary for the controller 310 to control the signal generator 330.

Figure 5:
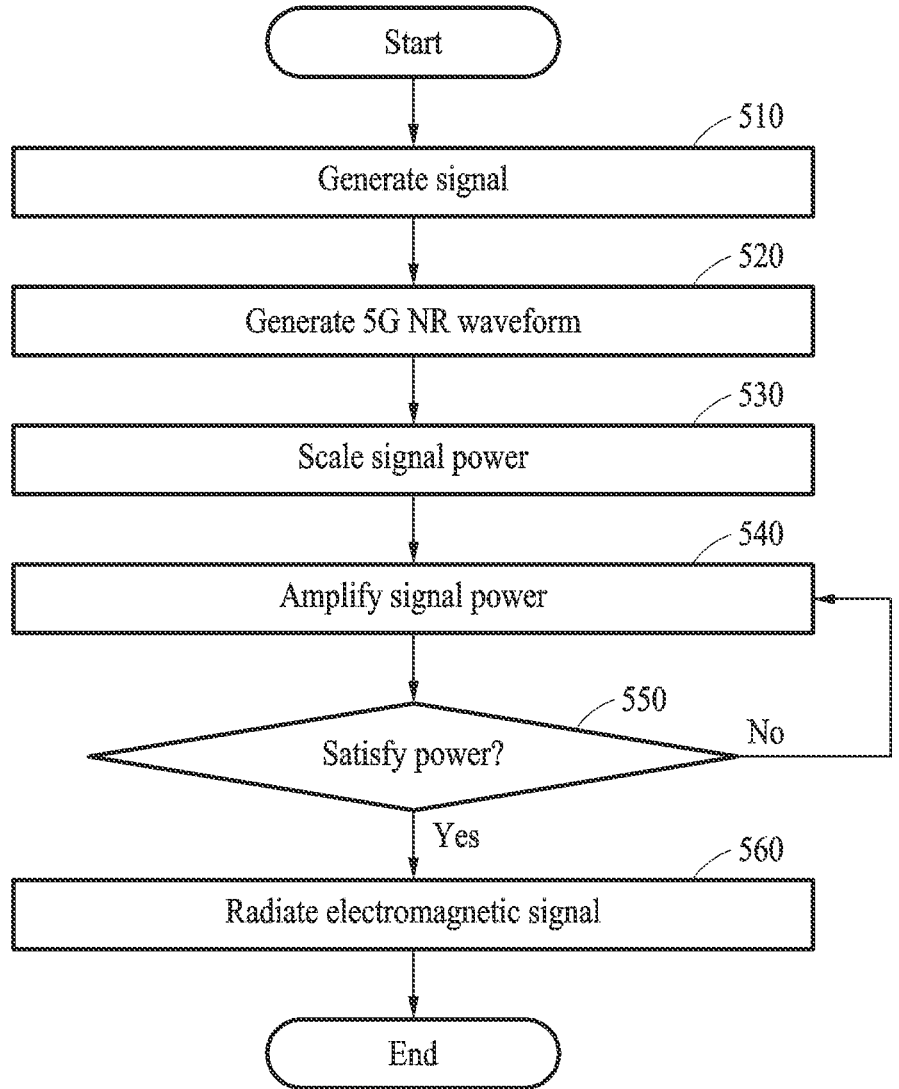
FIG. 5 is a flowchart illustrating an electromagnetic radiation method according to an embodiment.

FIG. 5 is a flowchart illustrating an electromagnetic radiation method according to an embodiment.

Referring to FIG. 5, according to various embodiments, an electromagnetic radiation apparatus (e.g., the electromagnetic radiation apparatus 300 of FIG. 3) may generate an electromagnetic wave (e.g., a 5G NR signal) and scale and amplify radiation power to irradiate the radiation power to a cell. A sequence of operations shown in FIG. 5 is an example for describing an operation method of the electromagnetic radiation apparatus 300, but is not limited thereto, and a plurality of operations may be performed in parallel or some operations may be omitted. For example, in a cell experiment with an electromagnetic wave except for a 5G NR signal, operation 520 may be omitted.

In operation 510, the electromagnetic radiation apparatus 300 may generate an electromagnetic wave.

In operation 520, the electromagnetic radiation apparatus 300 may generate a 5G NR signal by setting a flexible transmission structure (e.g., the flexible transmission structure of FIG. 1) in an electromagnetic wave.

In operation 530, the electromagnetic radiation apparatus 300 may scale radiation power of a 5G NR signal. A power scaling may be for performing a cell experiment by evaluating a 5G NR signal having a flexible transmission structure (e.g., the flexible transmission structure of FIG. 1) as a 5G NR signal configured only with a downlink.

In operation 540, the electromagnetic radiation apparatus 300 may amplify radiation power of a scaled 5G NR signal to achieve a target specific absorption rate (e.g., a 5G NR signal absorption rate of a cell).

In operation 550, the electromagnetic radiation apparatus 300 may check whether the radiation power of the scaled 5G NR signal amplified in operation 540 is suitable to achieve a target specific absorption rate.

In operation 560, the electromagnetic radiation apparatus 300 may irradiate (or radiate) the scaled 5G NR signal amplified in operation 540 to a cell container arranged in a radiation chamber (e.g., the radiation chamber 372 of FIG. 3).

Figure 6:
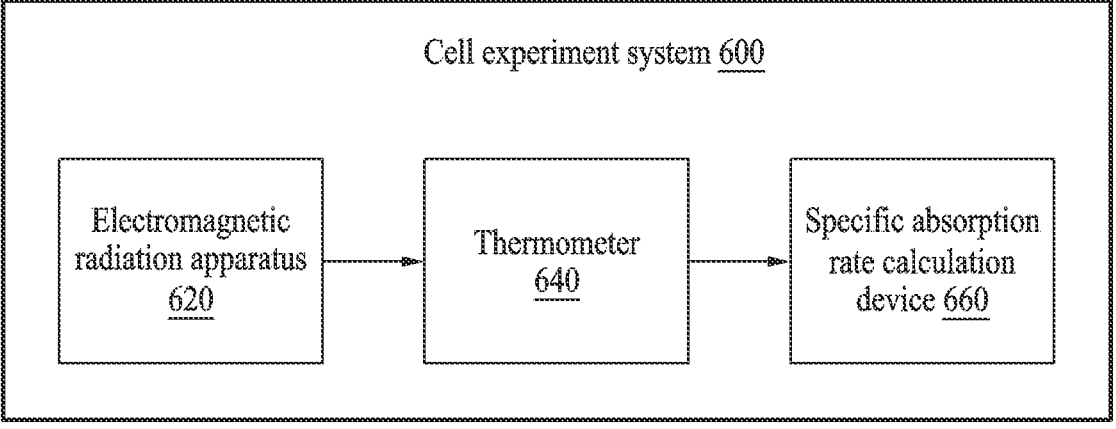
FIG. 6 is a schematic block diagram illustrating a cell experiment system according to an embodiment.

FIG. 6 is a schematic block diagram illustrating a cell experiment system according to an embodiment.

Referring to FIG. 6, according to various embodiments, a cell experiment system 600 may include an electromagnetic radiation apparatus 620, a thermometer 640, and a specific absorption rate calculation device 660.

According to various embodiments, the electromagnetic radiation apparatus 620 may actually be identical to the electromagnetic radiation apparatus 300 described with reference to FIGS. 3 to 5. Accordingly, further description thereof is not repeated herein.

According to various embodiments, the specific absorption rate calculation device 660 may calculate a specific absorption rate of cells by using a temperature of cells measured by the thermometer 640. For example, the specific absorption rate calculation device 660 may calculate a specific absorption rate of cells by using (e.g., the specific absorption rate calculation method of Equation 1) a rate of temperature change of cells immediately after irradiating an electromagnetic wave to the cells.

Figure 7:
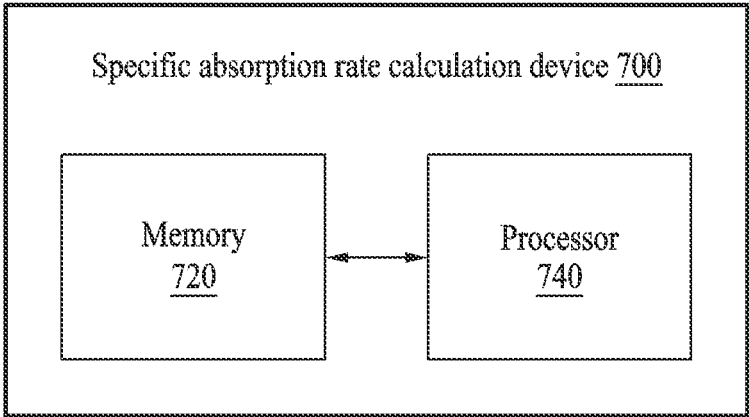
FIG. 7 is a schematic block diagram illustrating a specific absorption rate calculation device according to an embodiment.

FIG. 7 is a schematic block diagram illustrating a specific absorption rate calculation device according to an embodiment.

Referring to FIG. 7, according to various embodiments, a specific absorption rate calculation device 700 (e.g., the specific absorption rate calculation device 660 of FIG. 6) may include a memory 720 and a processor 740.

The memory 720 may store instructions (e.g., a program) executable by the processor 740. For example, the instructions may include instructions for executing an operation of the processor 740 and/or an operation of each component of the processor 740.

According to various example embodiments, the memory 720 may be implemented as a volatile memory device or a non-volatile memory device. The volatile memory device may be implemented as dynamic random-access memory (DRAM), static random-access memory (SRAM), thyristor RAM (T-RAM), zero capacitor RAM (Z-RAM), or twin transistor RAM (TTRAM). The non-volatile memory device may be implemented as electrically erasable programmable read-only memory (EEPROM), flash memory, magnetic RAM (MRAM), spin-transfer torque (STT)-MRAM, conductive bridging RAM (CBRAM), ferroelectric RAM (Fe-RAM), phase change RAM (PRAM), resistive RAM (RRAM), nanotube RRAM, polymer RAM (PoRAM), nano floating gate Memory (NFGM), holographic memory, a molecular electronic memory device, and/or insulator resistance change memory.

The processor 740 may execute computer-readable code (e.g., software) stored in the memory 720 and instructions triggered by the processor 740. "The processor 740" may be a data processing device implemented by hardware including a circuit having a physical structure to perform desired operations. The desired operations may include code or instructions included in a program. For example, the hardware-implemented data processing device may include a microprocessor, a CPU, a processor core, a multi-core processor, a multiprocessor, an application-specific integrated circuit (ASIC), and a field-programmable gate array (FPGA).

According to various example embodiments, operations performed by the processor 740 may be substantially the same as the operations performed by the specific absorption rate calculation device 660 described with reference to FIG. 6. Accordingly, further description thereof is not repeated herein.

The components described in the embodiments may be implemented by hardware components including, for example, at least one digital signal processor (DSP), a processor, a controller, an ASIC, a programmable logic element, such as an FPGA, other electronic devices, or combinations thereof. At least some of the functions or the processes described in the embodiments may be implemented by software, and the software may be recorded on a recording medium. The components, the functions, and the processes described in the embodiments may be implemented by a combination of hardware and software.

The example embodiments described herein may be implemented using a hardware component, a software component and/or a combination thereof. A processing device may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described devices may be configured to act as one or more software modules in order to perform the operations of the above-described embodiment, or vice versa.

As described above, although the example embodiments have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. An electromagnetic radiation apparatus comprising:

a signal generator configured to generate a first electromagnetic signal configured with an uplink and a downlink and scale and radiate power of the first electromagnetic signal in order to evaluate the first electromagnetic signal as a second electromagnetic signal configured only with a downlink; and a radiation chamber in which cell containers configured with cells are arranged in a circle in order to evenly irradiate a scaled first electromagnetic signal to the cells;

wherein the signal generator is configured to scale the power of the first electromagnetic signal by using a ratio of a number of downlink symbols per frame to a total number of symbols per frame of the first electromagnetic signal.

2. The electromagnetic radiation apparatus of claim 1, further comprising a controller configured to control the signal generator, wherein the signal generator is configured to amplify and radiate power of the scaled first electromagnetic signal under control by the controller.

3. The electromagnetic radiation apparatus of claim 1, wherein the first electromagnetic signal comprises the fifth-generation (5G) new radio (NR) signal configured with an uplink and a downlink, and the second electromagnetic signal comprises a 5G NR signal configured only with a downlink.

4. The electromagnetic radiation apparatus of claim 1, wherein the signal generator is configured to stop operating when a size of a reflected signal generated inside the signal generator exceeds a specific level.

5. The electromagnetic radiation apparatus of claim 1, wherein a bottom surface of the radiation chamber is configured with metal.

6. The electromagnetic radiation apparatus of claim 1, further comprising an incubator configured to maintain temperature and humidity for culturing the cells.

7. The electromagnetic radiation apparatus of claim 6, wherein the radiation chamber is disposed inside the incubator.

8. The electromagnetic radiation apparatus of claim 7, wherein the radiation chamber comprises a fan configured to circulate air inside the incubator.

9. The electromagnetic radiation apparatus of claim 1, further comprising a cooler configured to control a temperature increase of the cell containers caused by an absorption of an electromagnetic wave by the cells.

10. The electromagnetic radiation apparatus of claim 9, wherein the cooler comprises a pipe in which cooling water flows, and the pipe is installed below a bottom surface of the radiation chamber.

11. An electromagnetic radiation method comprising:

generating a first electromagnetic signal configured with an uplink and a downlink;

scaling power of the first electromagnetic signal in order to evaluate the first electromagnetic signal as a second electromagnetic signal configured only with a downlink;

arranging cell containers configured with cells in a circle in order to evenly irradiate a scaled first electromagnetic signal to the cells; and radiating the scaled first electromagnetic signal towards the cell containers;

wherein the scaling of the power of the first electromagnetic signal comprises using a ratio of a number of downlink symbols per frame to a total number of symbols per frame of the first electromagnetic signal.

12. The electromagnetic radiation method of claim 11, further comprising amplifying power of the scaled first electromagnetic signal, wherein the radiating of the scaled first electromagnetic signal comprises radiating an amplified first electromagnetic signal.

13. The electromagnetic radiation method of claim 11, wherein the first electromagnetic signal comprises the fifth-generation (5G) new radio (NR) signal configured with an uplink and a downlink, and the second electromagnetic signal comprises a 5G NR signal configured only with a downlink.

14. The electromagnetic radiation method of claim 12, further comprising stopping the amplifying of the power of the scaled first electromagnetic signal when a size of a reflected signal generated in a process of amplifying and radiating an electromagnetic signal exceeds a specific level.

15. The electromagnetic radiation method of claim 11, further comprising maintaining temperature and humidity for culturing the cells.

16. The electromagnetic radiation method of claim 11, further comprising controlling a temperature increase of the cell containers caused by an absorption of an electromagnetic wave by the cells.

17. The electromagnetic radiation method of claim 16, wherein the controlling of the temperature increase comprises cooling the cell containers by disposing a pipe in which cooling water flows adjacent to bottom surfaces of the cell containers.

18. A cell experiment system comprising:

the electromagnetic radiation apparatus of claim 1;

a thermometer configured to measure a temperature of cells which changes due to an irradiation of an electromagnetic wave generated by the electromagnetic radiation apparatus to the cells; and a specific absorption rate calculation device configured to calculate a specific absorption rate of the cells, wherein the specific absorption rate calculation device comprises:

a memory comprising instructions; and a processor electrically connected to the memory and configured to execute the instructions, wherein the processor, when the instructions are executed by the processor, is configured to calculate the specific absorption rate of the cells based on a rate of temperature change of the cells.

* * * * *